(12) United States Patent
Kamon

(10) Patent No.: US 10,939,799 B2
(45) Date of Patent: Mar. 9, 2021

(54) IMAGE PROCESSING APPARATUS, ENDOSCOPE SYSTEM, IMAGE PROCESSING METHOD, IMAGE PROCESSING PROGRAM, AND RECORDING MEDIUM

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 295 days.

(21) Appl. No.: 16/131,020

(22) Filed: Sep. 13, 2018

(65) Prior Publication Data

US 2019/0008362 A1  Jan. 10, 2019

Related U.S. Application Data

(63) Continuation of application No. PCT/JP2017/004893, filed on Feb. 10, 2017.

(30) Foreign Application Priority Data

Mar. 14, 2016  (JP) .............................. JP2016-049422

(51) Int. Cl.
*A61B 1/00* (2006.01)
*G06T 7/00* (2017.01)
(Continued)

(52) U.S. Cl.
CPC ...... *A61B 1/00009* (2013.01); *A61B 1/00006* (2013.01); *A61B 1/063* (2013.01);
(Continued)

(58) Field of Classification Search
CPC . A61B 1/00009; A61B 1/00006; A61B 1/063; A61B 1/3137; A61B 5/1459;
(Continued)

(56) References Cited

U.S. PATENT DOCUMENTS

| 5,757,877 A | 5/1998 | Wilting |
| 2009/0147096 A1 | 6/2009 | Yamaguchi et al. |

(Continued)

FOREIGN PATENT DOCUMENTS

| JP | 2009000236 | 1/2009 |
| JP | 2009153969 | 7/2009 |

(Continued)

OTHER PUBLICATIONS

"Written Opinion of the International Searching Authority (Form PCT/ISA/237) of PCT/JP2017/004893," dated May 9, 2017, with English translation thereof, pp. 1-11.

(Continued)

*Primary Examiner* — Eric F Winakur
*Assistant Examiner* — Abid A Mustansir
(74) *Attorney, Agent, or Firm* — JCIPRNET

(57) ABSTRACT

It is an object of the present invention to provide an image processing apparatus, an endoscope system, an image processing method, an image processing program, and a recording medium capable of accurately estimating blood vessel information. An image processing apparatus according to an aspect of the present invention includes: an image acquisition unit that acquires an image of a living body; a blood vessel index value calculation unit that calculates a blood vessel index value of the living body from the acquired image; a blood vessel density calculation unit that calculates a blood vessel density of the living body from the acquired image; a blood vessel index value correction unit that corrects the calculated blood vessel index value according to the calculated blood vessel density; and a blood vessel information estimation unit that estimates blood vessel information of the living body based on the corrected blood vessel index value.

19 Claims, 12 Drawing Sheets

(51) Int. Cl.
    *A61B 1/06*     (2006.01)
    *A61B 1/313*    (2006.01)
    *A61B 5/1459*   (2006.01)

(52) U.S. Cl.
    CPC .......... *A61B 1/3137* (2013.01); *A61B 5/1459* (2013.01); *G06T 7/0012* (2013.01); *G06T 2207/10024* (2013.01); *G06T 2207/10068* (2013.01); *G06T 2207/30101* (2013.01)

(58) Field of Classification Search
    CPC ......... G06T 7/0012; G06T 2207/10068; G06T 2207/30101; G06T 2207/10024
    See application file for complete search history.

(56) References Cited

U.S. PATENT DOCUMENTS

| | | | |
|---|---|---|---|
| 2010/0073731 A1 | 3/2010 | Takei et al. | |
| 2011/0077462 A1 | 3/2011 | Saitou et al. | |
| 2011/0112362 A1 | 5/2011 | Minetoma | |
| 2011/0237882 A1 | 9/2011 | Saito | |
| 2011/0237915 A1 | 9/2011 | Yamaguchi | |
| 2011/0245642 A1 | 10/2011 | Minetoma | |
| 2012/0078044 A1 | 3/2012 | Yamaguchi et al. | |
| 2012/0190922 A1* | 7/2012 | Kaku .................. A61B 1/0005 600/109 |
| 2013/0018242 A1 | 1/2013 | Yamaguchi et al. | |
| 2013/0030268 A1 | 1/2013 | Saito | |

FOREIGN PATENT DOCUMENTS

| | | | |
|---|---|---|---|
| JP | 2011194182 | | 10/2011 |
| JP | 2011217798 | | 11/2011 |
| JP | 2011218135 | | 11/2011 |
| JP | 2012071012 | | 4/2012 |
| JP | 2013022341 | | 2/2013 |
| JP | 2013202167 A | * | 10/2013 |
| JP | 5457247 | | 4/2014 |
| JP | 2014166590 | | 9/2014 |

OTHER PUBLICATIONS

"International Search Report (Form PCT/ISA/210) of PCT/JP2017/004893," dated May 9, 2017, with English translation thereof, pp. 1-5.

"Office Action of Japan Counterpart Application," dated Feb. 6, 2019, with English translation thereof, p. 1-p. 5.

"Search Report of Europe Counterpart Application", dated Mar. 7, 2019, p. 1-p. 8.

* cited by examiner

IMAGE PROCESSING APPARATUS, ENDOSCOPE SYSTEM, IMAGE PROCESSING METHOD, IMAGE PROCESSING PROGRAM, AND RECORDING MEDIUM

CROSS-REFERENCE TO RELATED APPLICATIONS

This application is a Continuation of PCT International Application No. PCT/JP2017/004893 filed on Feb. 10, 2017, which claims priority under 35 U.S.C § 119(a) to Japanese Patent Application No. 2016-049422 filed on Mar. 14, 2016. Each of the above application(s) is hereby expressly incorporated by reference, in its entirety, into the present application.

BACKGROUND OF THE INVENTION

1. Field of the Invention

The present invention relates to an image processing apparatus, an endoscope system, an image processing method, an image processing program, and a recording medium, and in particular, to an image processing apparatus for estimating blood vessel information of a living body, an endoscope system, an image processing method, an image processing program, and a recording medium.

2. Description of the Related Art

In the field of medical image processing, information regarding a living body is acquired by processing an image of the living body, and the acquired information is used for diagnosis. For example, JP5457247B and JP2011-194182A describe calculating the blood vessel depth and the oxygen saturation based on the brightness ratio between image signals having different wavelength ranges. JP2011-194182A also describes setting a region of interest based on the feature amount, such as a blood vessel thickness, and highlighting the region of interest. JP2009-153969A describes correcting image blur due to the depth of an object by performing filtering processing using an inverse function of a point spread function (PSF).

SUMMARY OF THE INVENTION

In an image obtained by imaging blood vessels, the blood vessels interfere with each other because the observation light scatters in the living body. This influences the blood vessel contrast or the like. The degree of such interference changes depending on the density of blood vessels. Therefore, in the case of estimating blood vessel information from information such as the blood vessel contrast, it is not possible to accurately estimate the blood vessel information unless the influence of interference according to the blood vessel density is considered. In the conventional techniques described in JP5457247B, JP2011-194182A, and JP2009-153969A, however, the influence of interference according to the blood vessel density has not been taken into consideration. As a result, it has been impossible to accurately estimate blood vessel information, such as the blood vessel depth.

The present invention has been made in view of such circumstances, and it is an object of the present invention to provide an image processing apparatus, an endoscope system, an image processing method, and an image processing program capable of accurately estimating blood vessel information, and a recording medium on which such an image processing program is recorded.

In order to achieve the aforementioned object, an image processing apparatus according to a first aspect of the present invention comprises: an image acquisition unit that acquires an image of a living body; a blood vessel index value calculation unit that calculates a blood vessel index value of the living body from the acquired image; a blood vessel density calculation unit that calculates a blood vessel density of the living body from the acquired image; a blood vessel index value correction unit that corrects the calculated blood vessel index value according to the calculated blood vessel density; and a blood vessel information estimation unit that estimates blood vessel information of the living body based on the corrected blood vessel index value.

In the image processing apparatus according to the first aspect, the blood vessel index value is corrected according to the blood vessel density in consideration of the influence of interference according to the blood vessel density, and the blood vessel information of the living body is estimated based on the corrected blood vessel index value. Therefore, blood vessel information can be accurately estimated. In the first aspect, the image of the living body may be acquired by an imaging device, or a captured image may be acquired through a network or a recording medium.

According to a second aspect, the image processing apparatus according to the first aspect further comprises a relationship information storage unit that stores relationship information indicating a relationship between the blood vessel density and the blood vessel index value, and the blood vessel index value correction unit corrects the calculated blood vessel index value based on the stored relationship information. The second aspect defines a method of correcting the blood vessel index value.

According to a third aspect, in the image processing apparatus according to the second aspect, the relationship information storage unit stores relationship information corresponding to a range of observation light emitted to the living body, the image acquisition unit acquires range information indicating the range of the observation light at the time of capturing the image, and the blood vessel index value correction unit corrects the blood vessel index value based on relationship information that is selected from the stored relationship information based on the acquired range information. In the third aspect, considering that the relationship between the blood vessel density and the blood vessel index value differs depending on the range of the observation light, the blood vessel index value is corrected based on the relationship information corresponding to the range of the observation light. In this manner, it is possible to accurately correct the blood vessel index value and to accurately estimate the blood vessel information based on the corrected blood vessel index value. In the third aspect, the range information may be acquired together with the image using a method, such as being recorded in the header portion of the image file, or may be acquired separately from the image. In the third aspect, it is preferable that the relationship information for each range of the observation light is stored as "relationship information corresponding to the range of the observation light" and the blood vessel index value is corrected using the relationship information.

According to a fourth aspect, in the image processing apparatus according to any one of the first to third aspects, the image acquisition unit acquires a plurality of images having different ranges of observation light emitted to the living body, and the blood vessel index value calculation unit calculates the blood vessel index value using the plurality of acquired images. In the fourth aspect, considering that the degree of absorption and scattering in the living body differs depending on the range of the observation light, the blood vessel index value is calculated using a plurality of images having different ranges of observation light. In the fourth aspect, "a plurality of images having different ranges of observation light" can be acquired by sequentially switching the wavelengths of a plurality of narrowband observation light beams. In addition, the observation light can also be acquired by sequentially switching band pass filters having different transmission wavelength ranges as wide ranges. The wavelength of "narrowband observation light" can be, for example, a wavelength selected from red, blue, green, and violet. The wavelength of "broadband observation light" can be, for example, white (wavelength in a range of a plurality of colors). However, the wavelength of "narrowband observation light" and the wavelength of "broadband observation light" are not limited thereto.

According to a fifth aspect, the image processing apparatus according to any one of the first to fourth aspects further comprises a blood vessel selection unit that selects a target blood vessel, for which the blood vessel index value is to be calculated, in the acquired image. In the fifth aspect, a blood vessel itself may be individually designated as a target blood vessel, or a blood vessel included in the designated region may be designated as a target blood vessel. In the fifth aspect, the calculation of the blood vessel density and the estimation of the blood vessel information may be performed for the target blood vessel selected in this manner or the target blood vessel included in the designated region.

According to a sixth aspect, in the image processing apparatus according to the fifth aspect, the blood vessel selection unit selects the target blood vessel based on a user's instruction input for the acquired image. According to the sixth aspect, the user can calculate a blood vessel index value for a desired target blood vessel. Also in the sixth aspect, similarly to the fifth aspect, a blood vessel itself may be individually designated as a target blood vessel, or a blood vessel included in the designated region may be designated as a target blood vessel. In addition, the calculation of the blood vessel density and the estimation of the blood vessel information may be performed for the target blood vessel selected in this manner or the target blood vessel included in the selected region.

According to a seventh aspect, in the image processing apparatus according to any one of the first to sixth aspects, the blood vessel index value includes at least one of a contrast of a blood vessel of the living body, a brightness value of a blood vessel portion, or color information of a blood vessel portion. The seventh aspect defines a specific item of the blood vessel index value.

According to an eighth aspect, in the image processing apparatus according to any one of the first to seventh aspects, the blood vessel information includes at least one of a depth of a blood vessel of the living body, a thickness of a blood vessel, a blood volume, or an oxygen saturation of a blood vessel. The eighth aspect defines a specific item of the blood vessel information.

In order to achieve the aforementioned object, an endoscope system according to a ninth aspect of the present invention comprises: a light source that emits observation light to a living body; an imaging unit that captures an image of the living body under the emitted observation light; and the image processing apparatus according to any one of the first to eighth aspects. The image processing apparatus acquires the image captured by the imaging unit. Since the ninth aspect defines the endoscope system including the endoscope apparatus that acquires the image of the living body and the image processing apparatus that processes the acquired image, it is possible to accurately estimate blood vessel information in the same manner as in the first aspect.

In order to achieve the aforementioned object, an image processing method according to a tenth aspect of the present invention comprises: an image acquisition step of acquiring an image of a living body; a blood vessel index value calculation step of calculating a blood vessel index value of the living body from the acquired image; a blood vessel density calculation step of calculating a blood vessel density of the living body from the acquired image; a blood vessel index value correction step of correcting the calculated blood vessel index value according to the calculated blood vessel density; and a blood vessel information estimation step of estimating blood vessel information of the living body based on the corrected blood vessel index value. According to the image processing method according to the tenth aspect, it is possible to accurately estimate blood vessel information in the same manner as in the first aspect. The image processing method according to the tenth aspect may further include the same configuration as in the second to eighth aspects.

In order to achieve the aforementioned object, an image processing program according to an eleventh aspect of the present invention causes an image processing apparatus to execute the image processing method according to the tenth aspect. According to the image processing program according to the eleventh aspect, it is possible to accurately estimate blood vessel information in the same manner as in the first and tenth aspects.

In order to achieve the aforementioned object, in a non-transitory recording medium according to a twelfth aspect of the present invention, a computer readable code of the image processing program according to the eleventh aspect is recorded. According to the recording medium according to twelfth aspect, it is possible to execute the image processing program capable of accurately estimating blood vessel information. As examples of the non-transitory recording medium, a magneto-optical recording medium, such as a compact disc and a hard disk, and various kinds of semiconductor memories can be mentioned. However, the non-transitory recording medium according to the present invention is not limited to these examples.

As described above, according to the image processing apparatus, the endoscope system, the image processing method, the image processing program, and the recording medium of the present invention, it is possible to accurately estimate blood vessel information.

DESCRIPTION OF THE PREFERRED EMBODIMENTS

Hereinafter, embodiments of an image processing apparatus, an endoscope system, an image processing method, an image processing program, and a recording medium according to the present invention will be described with reference to the accompanying diagrams.

First Embodiment

Figure 1:
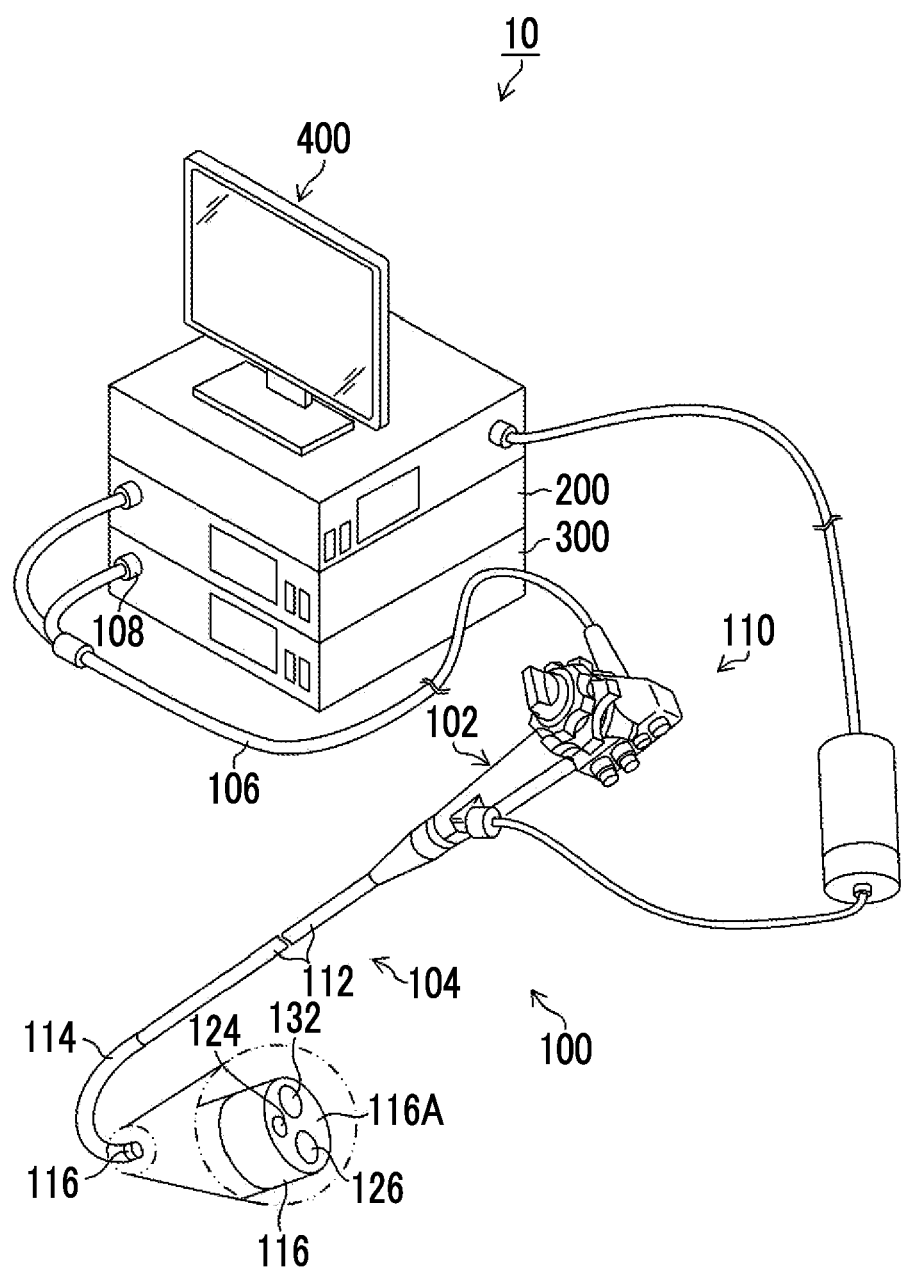
FIG. 1 is an external view showing an endoscope system according to a first embodiment.
Figure 2:
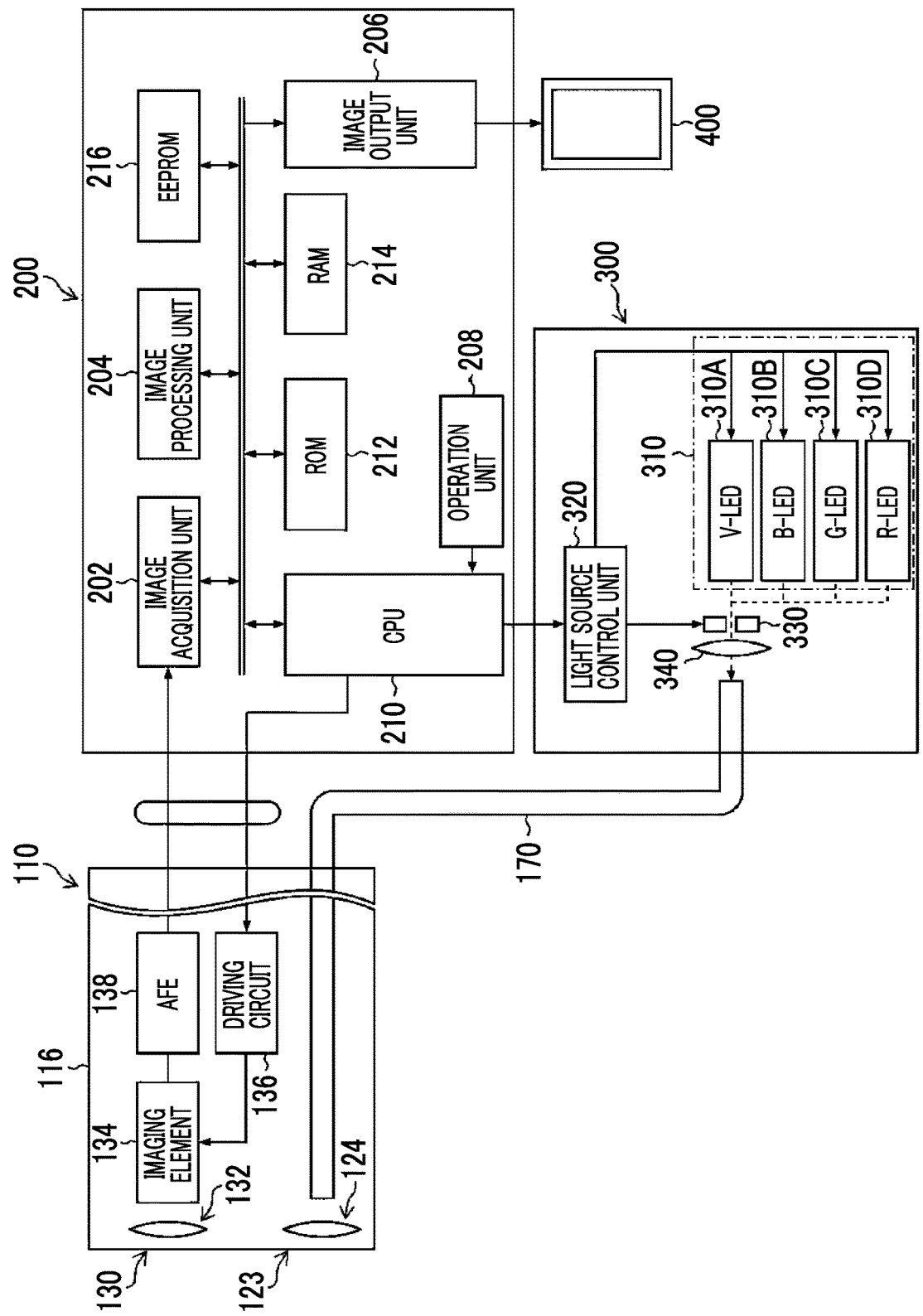
FIG. 2 is a block diagram showing the schematic configuration of an endoscope system.

FIG. 1 is an external view showing an endoscope system 10 (endoscope system) according to a first embodiment, and FIG. 2 is a block diagram showing the main part configuration of the endoscope system 10. As shown in FIGS. 1 and 2, the endoscope system 10 includes an endoscope apparatus 100 configured to include an endoscope main body 110 (imaging unit), an endoscope processor 200 (image processing apparatus), a light source device 300 (light source), and a monitor 400.

<Configuration of an Endoscope Main Body>

The endoscope main body 110 includes a hand operation portion 102 and an insertion part 104 connected to the hand operation portion 102. A doctor grips and operates the hand operation portion 102, and inserts the insertion part 104 into the body of the subject to observe the inside of the body. The insertion part 104 is configured to include a soft portion 112, a bending portion 114, and a distal end rigid portion 116 in this order from the hand operation portion 102 side. An imaging optical system 130 (imaging unit), an illumination unit 123, a forceps port 126, and the like are provided in the distal end rigid portion 116.

During observation or treatment, observation light of a range (refer to FIGS. 3 and 4) to be described later can be emitted through an observation light lens 124 of the illumination unit 123 by operating an operation unit 208 (refer to FIG. 2). In addition, by operating the operation unit 208, cleaning water is discharged from a water supply nozzle (not shown), so that an imaging lens 132 and the observation light lens 124 can be cleaned. A pipe line (not shown) communicates with a forceps port 126 opened at a distal end side end surface 116A of the distal end rigid portion 116, and a treatment tool (not shown) is inserted through the pipe line and appropriately moves back and forth to perform required measures.

On the distal end side end surface 116A, the observation light lens 124 of the illumination unit 123 is provided adjacent to the imaging lens 132. An exit end of a light guide 170, which will be described later, is disposed behind the observation light lens 124. The light guide 170 is inserted through the insertion part 104, the hand operation portion 102, and a universal cable 106, and the incidence end of the light guide 170 is disposed in a light guide connector 108.

As shown in FIGS. 1 and 2, the imaging lens 132 is disposed on the distal end side end surface 116A. Behind the imaging lens 132, a complementary metal oxide semiconductor (CMOS) type imaging element 134, a driving circuit 136, and an analog front end (AFE) 138 are disposed to output an image signal. An optical image of the subject is formed on the light receiving surface of the imaging element 134 by the imaging lens 132, and is converted into an electric signal. The electric signal is output to the endoscope processor 200 through a signal cable (not shown) and is converted into a video signal, and an observation image is displayed on the monitor 400 through an image output unit 206.

Figure 4:
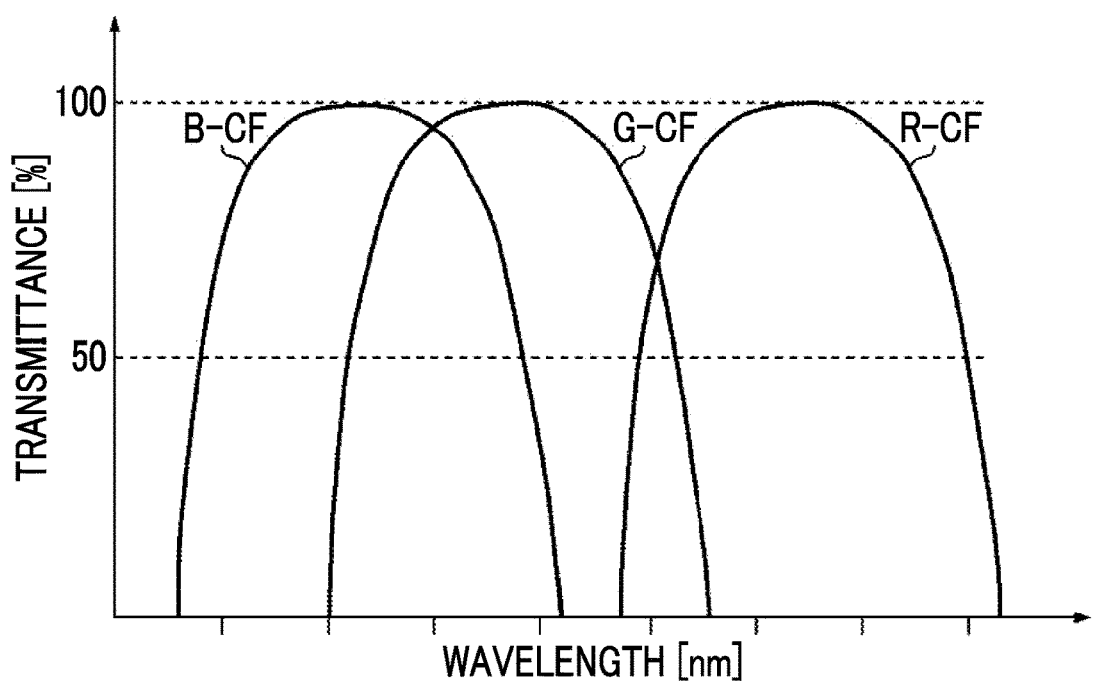
FIG. 4 is a diagram showing a relationship between the wavelength of a color filter and a transmittance.

The imaging element 134 described above is a color image pickup element, and includes a plurality of pixels configured to include a plurality of light receiving elements arranged in a matrix (in a two-dimensional manner) with a predetermined pattern arrangement (Bayer arrangement, G stripe RB complete checkered arrangement, X-Trans (registered trademark) arrangement, honeycomb arrangement, and the like). Each pixel includes a microlens, a color filter of red (R), green (G), or blue (B), and a photoelectric conversion unit (photodiode or the like). The imaging element 134 receives violet light to blue light in a B pixel (blue pixel) in which a B color filter B-CF is provided, receives green light in a G pixel (green pixel) in which a G color filter G-CF is provided, and receives red light in an R pixel (red pixel) in which an R color filter R-CF is provided. The transmittances of the R, G, and B color filters with respect to the wavelength are shown in FIG. 4.

The imaging optical system 130 can generate a color image from the signals of the red pixel, the green pixel, and the blue pixel. In the case of generating a color image, a demosaicing process (also referred to as demosaicing) according to the arrangement pattern of color filters is performed to generate a signal of insufficient color in each pixel by interpolation, so that all the pixels have signals of RGB colors. It is also possible to generate an image from pixel signals of any one color or two colors of red, green and blue.

In the first embodiment, a case where the imaging element 134 is a CMOS type imaging element will be described. However, the imaging element 134 may be a charge coupled device (CCD) type element.

<Configuration of a Light Source Device>

As shown in FIG. 2, the light source device 300 (light source) is configured to include a light source for observation light 310 (light source), a light source control unit 320, a stop 330, a condensing lens 340, and the like, and makes observation light incident on the light guide 170. The observation light is guided through the insertion part 104 by the light guide 170, and is emitted to the subject from the observation light lens 124 provided on the distal end side end surface 116A.

Figure 3:
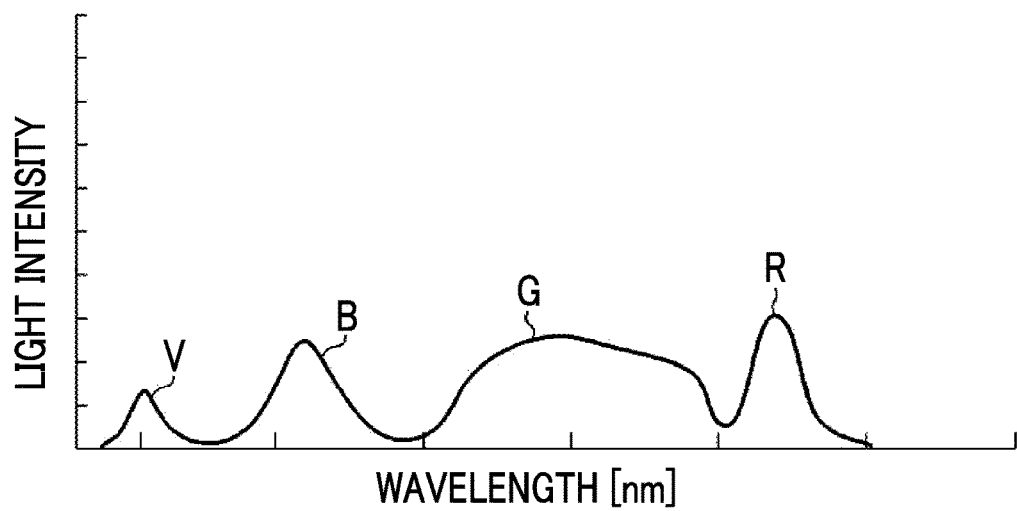
FIG. 3 is a diagram showing the wavelength of a light source.

In the present embodiment, as shown in FIG. 2, the light source 310 has light emitting diodes (LEDs) of four colors of a violet light emitting diode (V-LED) 310A that emits violet light, a blue light emitting diode (B-LED) 310B that emits blue light, a green light emitting diode (G-LED) 310C that emits green light, and a red light emitting diode (R-LED) 310D that emits red light. The spectrum shown in FIG. 3 is a spectrum in a case where the four LEDs emit light simultaneously (V: violet light, B: blue light, G: green light, R: red light). ON or OFF of these LEDs, the amount of light emission at the time of lighting, and the like can be individually controlled by the light source control unit 320, and a plurality of LEDs can be turned on at the same time, or only one LED can be turned on.

<Configuration of an Endoscope Processor>

Next, the configuration of the endoscope processor 200 will be described with reference to FIG. 2. In the endoscope processor 200, an image acquisition unit 202 (image input unit) receives an image signal output from the endoscope apparatus 100, and an image processing unit 204 (a blood vessel index value calculation unit, a blood vessel density calculation unit, a blood vessel index value correction unit, a blood vessel information estimation unit, and a blood vessel selection unit) performs required image processing. The result is output through the image output unit 206. As a result, an observation image is displayed on the monitor 400. These processes are performed under the control of a central processing unit (CPU) 210. The image acquisition unit 202, the image processing unit 204, and the image output unit 206 are, for example, electric circuits that operate under the control of the CPU 210. The CPU 210 or a control device, such as various processors provided separately from the CPU 210, executes an image processing program stored in storage means, such as a ROM 212, to operate as the image acquisition unit 202, the image processing unit 204, and the image output unit 206.

In addition to the image processing such as white balance adjustment, the image processing unit 204 performs switching or superimposed display of images to be displayed on the monitor 400, electronic zoom processing, display and switching of images according to the operation mode, extraction of a specific component (for example, a brightness signal) from the image signal, and the like. A computer readable code of an image processing program according to the present embodiment is recorded in a read only memory (ROM) 212 (non-transitory recording medium), and a random access memory (RAM) 214 is used as a temporary storage region for processing. In an electronically erasable and programmable read only memory (EEPROM) 216, information required for the processing performed by the CPU 210 or the image processing unit 204, such as relationship information (refer to FIGS. 13 and 16) to be described later, is stored in advance.

The endoscope processor 200 includes the operation unit 208. The operation unit 208 includes input devices such as a keyboard and a mouse (not shown), and the user can perform an operation, such as designation of a target blood vessel, through these input devices. Such an operation will be described later. The operation unit 208 includes an operation mode setting switch, a water supply instruction button, and the like (not shown), and it is possible to operate emission of observation light.

<Functional Configuration of an Image Processing Unit>

Figure 5:
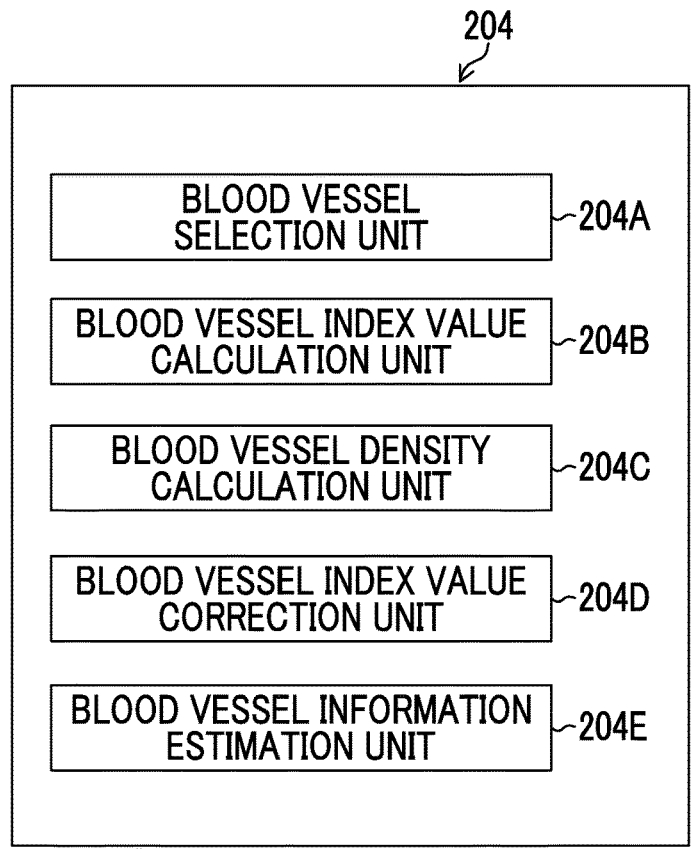
FIG. 5 is a diagram showing the functional configuration of an image processing unit.

FIG. 5 is a diagram showing the functional configuration of the image processing unit 204. The image processing unit 204 includes a blood vessel selection unit 204A that selects a target blood vessel for which a blood vessel index value and blood vessel information are to be calculated, a blood vessel index value calculation unit 204B that calculates a blood vessel index value, such as a blood vessel contrast, a blood vessel density calculation unit 204C that calculates a blood vessel density, a blood vessel index value correction unit 204D that corrects the blood vessel index value according to the calculated blood vessel density, and a blood vessel information estimation unit 204E that estimates blood vessel information based on the corrected blood vessel index value.

<Image Processing Procedure>

Figure 6:
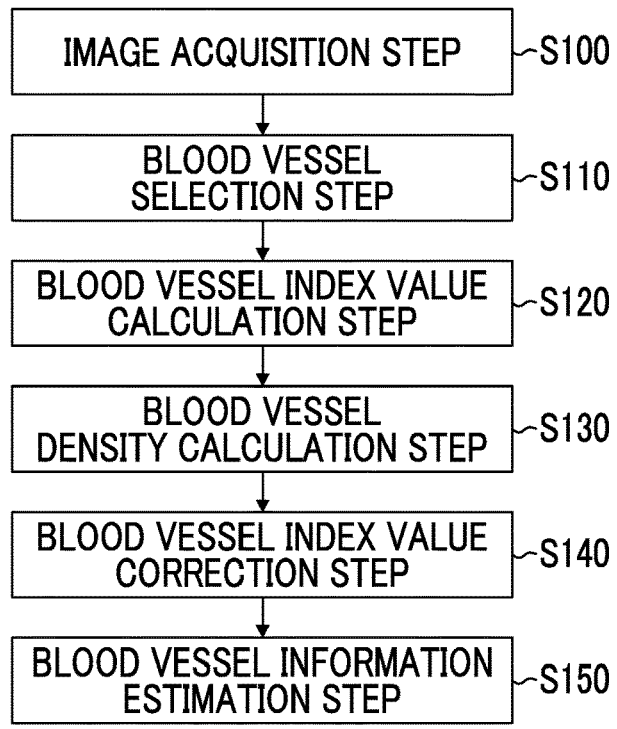
FIG. 6 is a flowchart showing the process of an image processing method according to the first embodiment.

Next, image processing in the endoscope system 10 having the above-described configuration will be described. FIG. 6 is a flowchart showing the procedure of image processing (image processing method) according to the first embodiment.

<Image Acquisition>

First, observation light of violet, blue, green, and red are emitted from the light source device 300 having the above-described configuration, and the imaging optical system 130 images the subject (living body) to acquire image signals of blue, green, and red (step S100: image acquisition step). The type of observation light to be emitted can be set according to an image to be acquired, and observation light beams of the respective colors may be emitted at the same time as necessary, or the ranges may be sequentially switched. In the endoscope system 10, it is possible to generate a color image using the image signals of three colors acquired in this manner, and it is possible to generate an image using the image signal of one color or two colors among the three colors. In addition, using the image signals of two or more colors among the three colors, it is also possible to generate an image subjected to difference processing and/or emphasis processing (for example, an image in which a blood vessel at a desired depth is emphasized). As described above, in the present embodiment, it is possible to acquire a plurality of images having different ranges of observation light.

<Selection of Target Blood Vessel>

Then, the image processing unit 204 (blood vessel selection unit 204A) selects a target blood vessel, for which a blood vessel index value is to be calculated, in the image acquired in step S100 (step S110: blood vessel selection step). The target blood vessel may be automatically selected by the image processing unit 204 without a user's instruction input, or may be selected based on a user's instruction input through the operation unit 208. In the case of automatically selecting the target blood vessel, blood vessels included in a partial region, such as the center of the image, may be selected, or blood vessels included in the entire region of the image may be selected. In addition, a blood vessel having a feature amount (for example, shape, thickness, and color) that satisfies designated conditions may be selected as the target blood vessel. The number of target blood vessels is not limited to one, and a plurality of target blood vessels may be designated.

Figure 7:
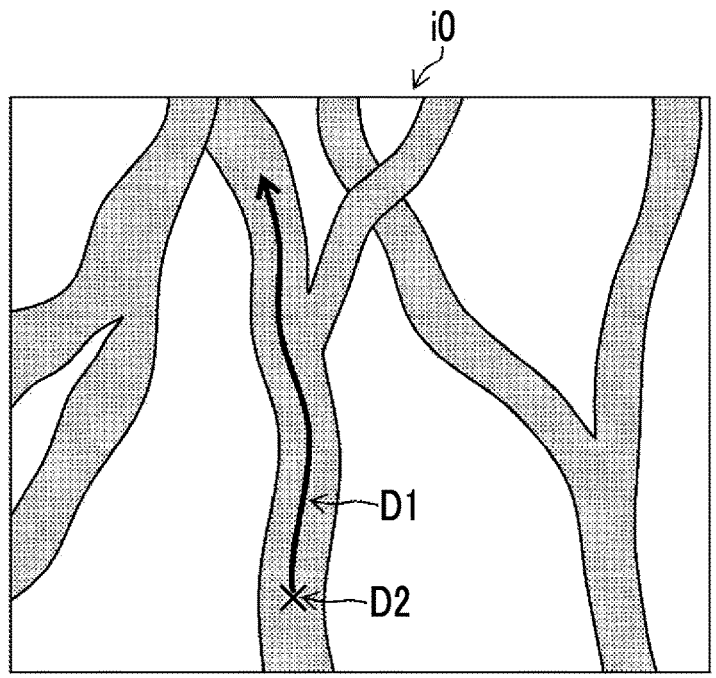
FIG. 7 is a diagram showing how a target blood vessel is selected based on a user's operation.
Figure 8:
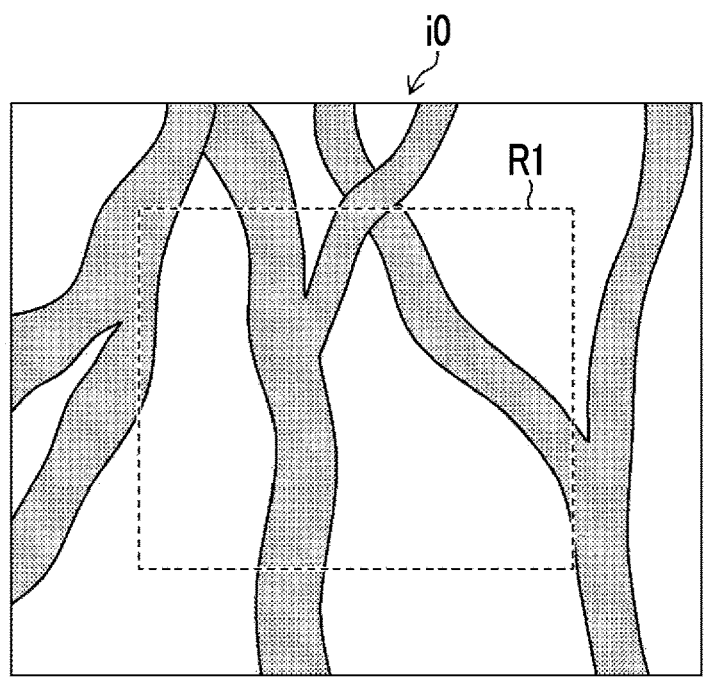
FIG. 8 is another diagram showing how a target blood vessel is selected based on a user's operation.

On the other hand, in the case of selecting the target blood vessel based on the user's instruction input, an image is displayed on the monitor 400, and the user's instruction input with respect to the displayed image is received through the operation device (a keyboard, a mouse, or the like) of the operation unit 208. In this case, as shown in FIG. 7, the user may directly select the target blood vessel using a method, such as clicking a blood vessel portion on an image i0 or moving a cursor along the blood vessel. Alternatively, as shown in FIG. 8, the user may designate a region of interest (ROI) on the image i0 so that a blood vessel included in the region of interest is selected as the target blood vessel. In FIG. 7, a curve D1 and a point D2 indicate the movement trajectory of the cursor and the start point thereof. In FIG. 8, a region R1 indicates a designated region of interest.

<Calculation of a Blood Vessel Index Value>

In a case where the target blood vessel is selected in step S110, the image processing unit 204 (blood vessel index value calculation unit 204B) calculates a blood vessel index value for the selected target blood vessel (step S120: blood vessel index value calculation step). As the blood vessel index value, at least one of the blood vessel contrast, the brightness value of the blood vessel portion, or the color information of the blood vessel portion can be mentioned. However, the blood vessel index value is not limited thereto. For example, as described in JP2015-91467A, a blood vessel region can be specified based on the image signal, and the blood vessel index value can be calculated from the image signal in the specified blood vessel region. Specifically, a B/G ratio image showing the brightness ratio between the blue signal and the green signal is generated based on the blue image signal and the green image signal acquired in the image acquisition step of step S100. In the B/G ratio image, a pixel region having a B/G ratio within a predetermined range is specified as a mucous membrane, and a pixel region having a B/G ratio outside the predetermined range is specified as a blood vessel.

In a case where the blood vessel and the mucous membrane are specified by the processing described above, the image processing unit 204 calculates the ratio between the brightness value of the blood vessel and the brightness value of the mucous membrane as a blood vessel contrast. In addition, by converting the image signals of RGB (red, green, and blue) in the blood vessel portion into the YCbCr format by the following Equations (1), (2), and (3), it is possible to calculate the brightness value (value of Y signal) of the blood vessel portion. In addition, it is possible to calculate the color information (R/G ratio, B/G ratio, and the like) of the blood vessel from the RGB image signals in the blood vessel portion.

$$Y=0.299 \times R+0.587 \times G+0.114 \times B \quad (1)$$

$$Cb=-0.169 \times R-0.331 \times G+0.5 \times B \quad (2)$$

$$Cr=0.5 \times R-0.419 \times G-0.081 \times B \quad (3)$$

<Calculation of a Blood Vessel Density>

Then, the image processing unit 204 (blood vessel density calculation unit 204C) calculates a blood vessel density (step S130: blood vessel density calculation step). The reason why the blood vessel density is calculated in step S130 is that the blood vessel index value changes according to the blood vessel density and accordingly it is necessary to correct the influence of the change in the blood vessel index value in the case of estimating the blood vessel information from the blood vessel index value. The influence of the blood vessel density on the blood vessel index value and the correction of the blood vessel index value based on the calculated blood vessel density will be described in detail later.

The blood vessel density can be calculated, for example, from the area of a blood vessel region occupied on the image after specifying the blood vessel region using the method described above. In a case where the number of blood vessels is the same but the thicknesses of the blood vessels are different, the degree of interference between blood vessels is also different. Therefore, it is preferable to calculate a density (area density) based on the area of blood vessels as described above instead of a density (number density) based on the number of blood vessels. In addition to calculating the blood vessel density from the area of the blood vessel portion in this manner, the blood vessel density may be calculated from the brightness value on the image (for example, the brightness value in the region of interest), or may be calculated based on a plurality of images having different observation light ranges. In the case of calculating the blood vessel density based on a plurality of images having different observation light ranges, for example, it is preferable to take a difference between an image based on long-wave observation light (for example, red) with almost no blood vessels and an image based on short-wave observation light (for example, blue and green) in which absorption due to blood vessels is large and accordingly the blood vessels are clearly shown.

<Correction of a Blood Vessel Index Value>

Then, the image processing unit 204 (blood vessel index value correction unit 204D) corrects the blood vessel index value according to the blood vessel density calculated in step S130 (step S140: blood vessel index value correction step).

<Influence of Blood Vessel Density on a Blood Vessel Index Value>

Figure 9:
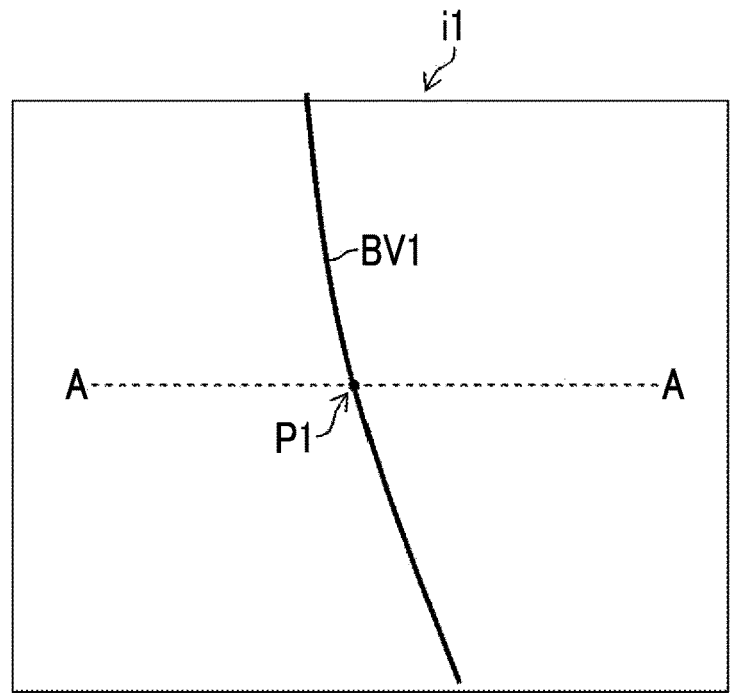
FIG. 9 is a diagram illustrating the influence of the blood vessel density on the brightness.
Figure 10:
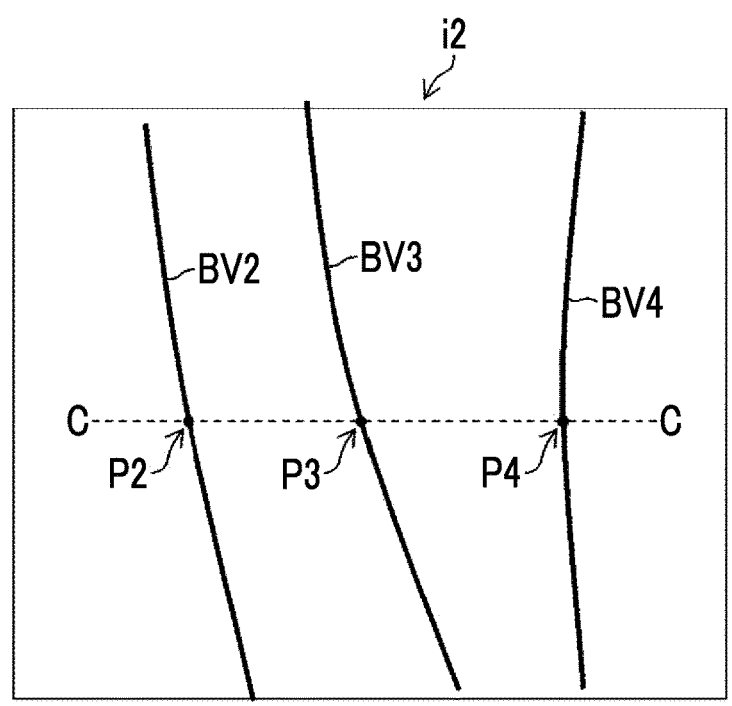
FIG. 10 is another diagram illustrating the influence of the blood vessel density on the brightness.
Figure 11:
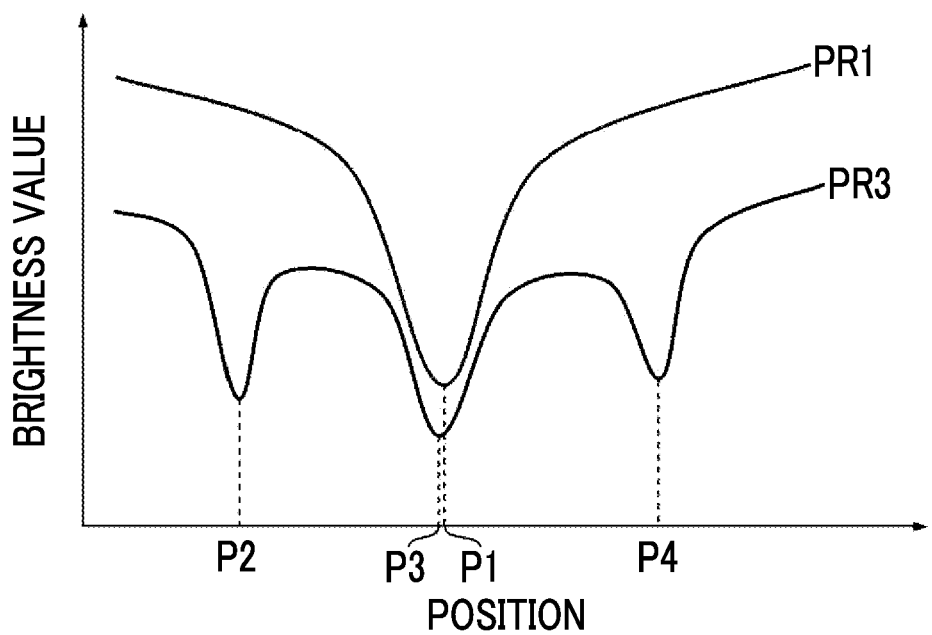
FIG. 11 is still another diagram illustrating the influence of the blood vessel density on the brightness.

Regarding the correction of the blood vessel index value, the influence of the blood vessel density on the blood vessel index value will be described first. Here, the brightness value of a blood vessel portion will be described as an example of the blood vessel index value. FIG. 9 is a diagram schematically showing an image i1 in which one blood vessel BV1 is shown, and FIG. 10 is a diagram schematically showing an image i2 in which three blood vessels BV2, BV3, and BV4 are shown. FIG. 11 is a diagram showing a brightness value PR1 in the A-A line portion in the image i1 and a brightness value PR3 in the C-C line portion in the image i2.

Figure 12:
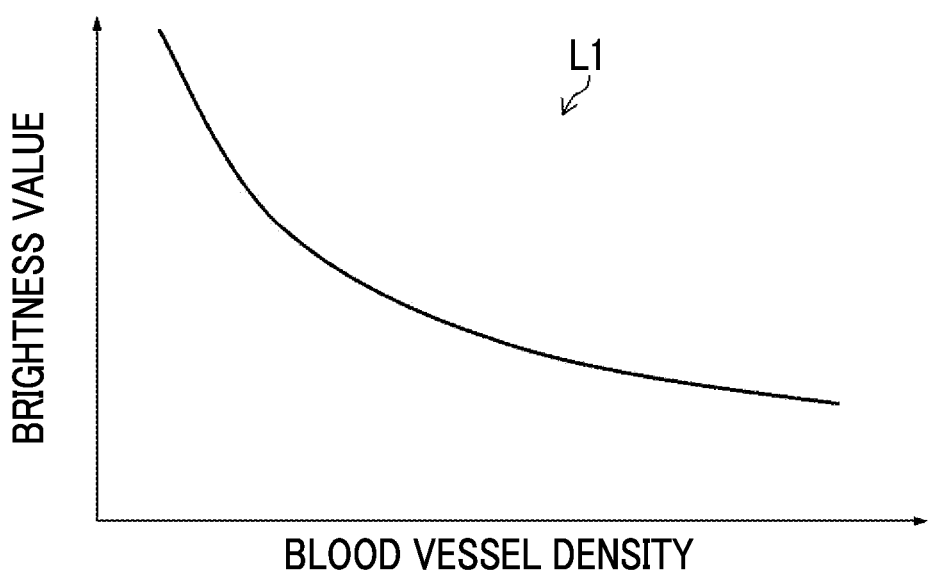
FIG. 12 is a conceptual diagram showing a change in brightness value due to the blood vessel density.

The signal of the blood vessel portion is observed spatially spread due to the scattering of light in the living body. Accordingly, in the brightness values PR1 and PR3 shown in FIG. 11, not only the brightness values in the blood vessel portion (positions of points P1 to P4 in FIGS. 9 and 10) but also the brightness values around the blood vessel portion change due to interference. This influence can be estimated by the peripheral blood vessel density, and the brightness value of the blood vessel portion decreases as the blood vessel density increases as shown by a curve L1 in FIG. 12. That is, as shown by a curve L2 in FIG. 13, the brightness value variation amount (absolute value) increases as the blood vessel density increases.

<Correction of a Blood Vessel Index Value According to Blood Vessel Density>

Figure 13:
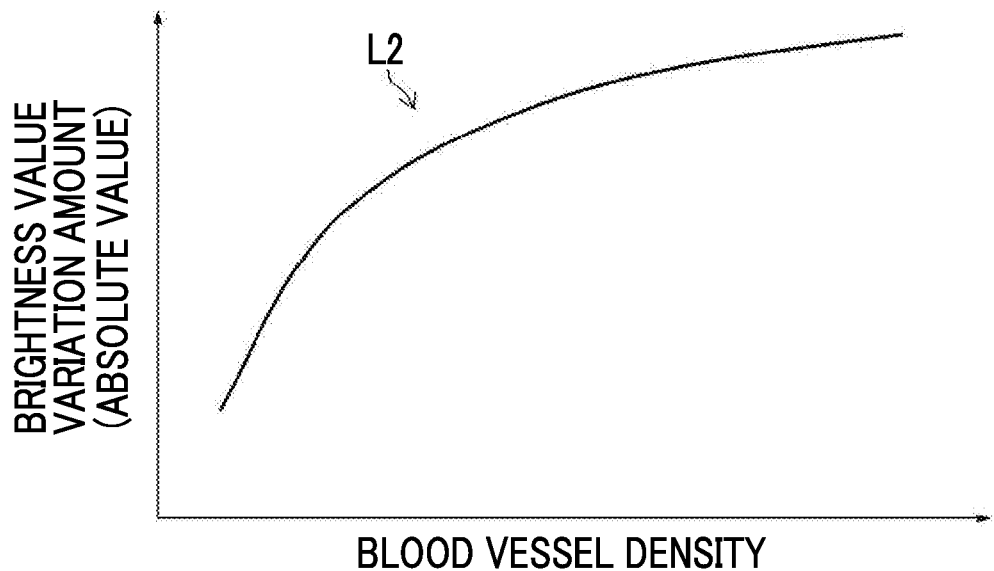
FIG. 13 is a conceptual diagram showing a relationship between the blood vessel density and the brightness value variation amount.
Figure 14:
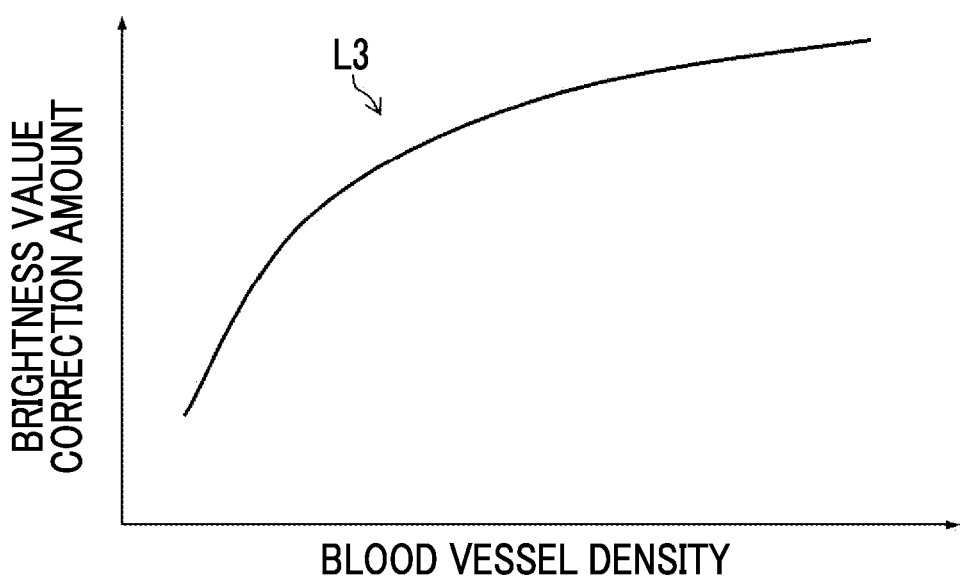
FIG. 14 is a diagram showing a brightness value correction amount according to the blood vessel density.
Figure 15:
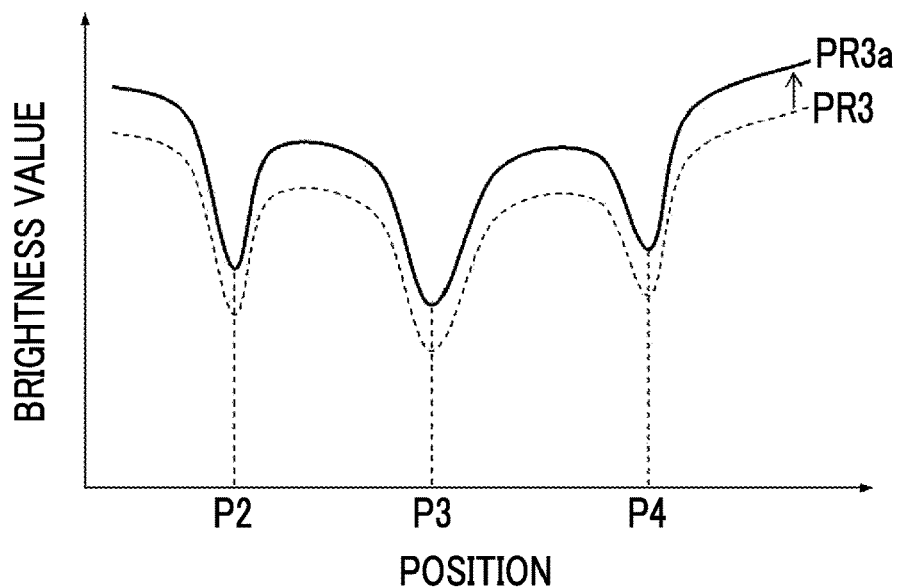
FIG. 15 is a diagram showing correction of a brightness value.

Since the blood vessel index value changes according to the blood vessel density as described above, it is necessary to correct the influence in the case of estimating the blood vessel information from the blood vessel index value, such as the brightness value of the blood vessel portion. In the first embodiment, therefore, a relationship between the blood vessel density and the brightness value variation amount (relationship information), such as that shown in the curve L2 in FIG. 13, is stored in the EEPROM 216 (relationship information storage unit), and the brightness value is corrected with reference to the relationship information. Specifically, the image processing unit 204 corrects the brightness value by adding a correction amount (the correction amount increases as the blood vessel density increases) corresponding to the relationship information (curve L2), such as a curve L3 in FIG. 14, to the brightness value before correction. FIG. 15 is a diagram showing such correction of the brightness value, and shows how the brightness value PR3 before correction (the brightness value in a case where there are three blood vessels as shown in FIGS. 10 and 11) is changed to PR3a by addition of the correction amount.

The relationship information may be experimentally created by using a phantom simulating blood vessels, or may be created by optical simulation, such as Monte Carlo simulation.

Figure 16:
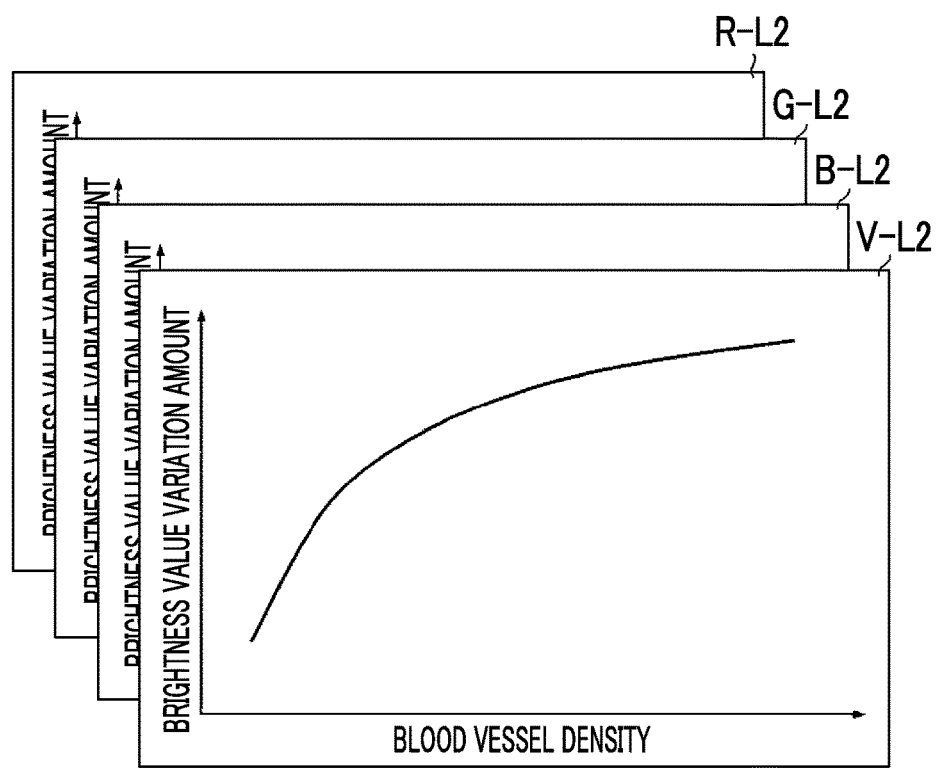
FIG. 16 is a diagram showing how relationship information according to the range of observation light is stored.

Since the variation in the brightness value due to the blood vessel density is caused by scattering of light, the scattering coefficient of the mucous membrane is different in a case where the range of the observation light is different, and the brightness value variation amount is also different. In general, the shorter the wavelength of the observation light, the higher the absorption coefficient of blood. Accordingly, the brightness value variation amount according to the blood vessel density also increases. Therefore, from such a point of view, relationship information (relationship information R-L2, G-L2, B-L2, and V-L2 of red, green, blue, and violet) for each range of observation light shown in FIG. 16 may be stored in the EEPROM 216 or the like, and correction may be performed with reference to the relationship information for each range. In the case of using the relationship information according to the range of observation light, information (range information) indicating the range of the observation light at the time of capturing an image may be recorded, for example, in the header portion of the image file, and the image processing unit 204 may correct the brightness value based on the relationship information selected with reference to the range information. Both the blue light and the violet light are received by the B pixel (blue pixel), the blue light and the violet light have information of different ranges. Therefore, there are four kinds of ranges of red, green, blue, and violet in which the variation in the brightness value can be taken into consideration. For this reason, as shown in FIG. 16, it is preferable to store relationship information for red, green, blue, and violet and use the four kinds of relationship information.

For the correction of the blood vessel index value, the case where the relationship between the blood vessel density and the brightness value variation amount is stored as the relationship information has been described. However, a correction amount (addition amount) corresponding to the brightness value variation amount, such as that shown in the curve L3 of FIG. 14, may be stored as relationship information. In addition, for the correction of the blood vessel index value, the case of correcting the brightness value has been described. However, in the case of correcting the contrast, relationship information (or a correction coefficient) for contrast correction may be stored, and multiplication of the correction coefficient based on the relationship information may be performed. In the case of correcting the color information, it is preferable to store relationship information (correction amount) for the image signal of each color (red, green, and blue) and add the correction amount based on the relationship information.

<Estimation of Blood Vessel Information>

After the blood vessel index value is corrected in step S140, the image processing unit 204 (blood vessel information estimation unit 204E) estimates the blood vessel information of the living body, such as a blood vessel thickness, a blood vessel depth, a blood volume, and oxygen saturation, based on the corrected blood vessel index value (step S150: blood vessel information estimation step). Estimation of blood vessel information is performed for the target blood vessel selected in step S110 or a region (region of interest or the like) including the target blood vessel. For the blood vessel depth and the oxygen saturation, for example, as described in JP2011-194182A, a correlation between the brightness ratio of the image signal and the oxygen saturation in the blood vessel and the blood vessel depth can be stored, and the blood vessel depth and the oxygen saturation can be estimated based on the correlation and the brightness value of each color after correction. For the blood vessel depth, for example, as described in JP2015-231576A, a correlation between the brightness ratio (B/G) of the image signal and the blood vessel depth (proportional relationship in which the brightness ratio B/G also increases as the blood vessel depth increases) can be stored, and the blood vessel depth can be estimated based on the correlation and the brightness value of each color after correction. For the blood volume and the oxygen saturation, for example, as described in JP2015-70369A, a correlation between the brightness ratio (B/G and R/G) of the image signal and the blood volume and the oxygen saturation can be stored, and the blood volume and the oxygen saturation can be estimated based on the correlation and the brightness value of each color after correction.

As described above, in the endoscope system 10 according to the first embodiment, the blood vessel index value is corrected according to the blood vessel density in consideration of the influence of interference according to the blood vessel density, and the blood vessel information of the living body is estimated based on the corrected blood vessel index value. Therefore, since the blood vessel information, such as the blood vessel depth, the blood vessel thickness, and the oxygen saturation, can be accurately estimated, it is possible to present information useful for diagnosis.

<Modification Examples of a Light Source Device and Image Acquisition>

Next, a modification example of the light source device in the first embodiment will be described. In the example shown in FIG. 2, the case has been described in which the light source device 300 includes violet, blue, green, and red LEDs and blue, green, and red color filters and a color image is acquired by demosaicing process (demosaicing). However, the light source device and the image acquisition in the present invention are not limited to those described above. Hereinafter, a light source device having another configuration will be described. In a modification example shown in FIGS. 17 and 18, the same elements as in FIG. 2 are denoted by the same reference numerals, and the detailed description thereof will be omitted.

Figure 17:
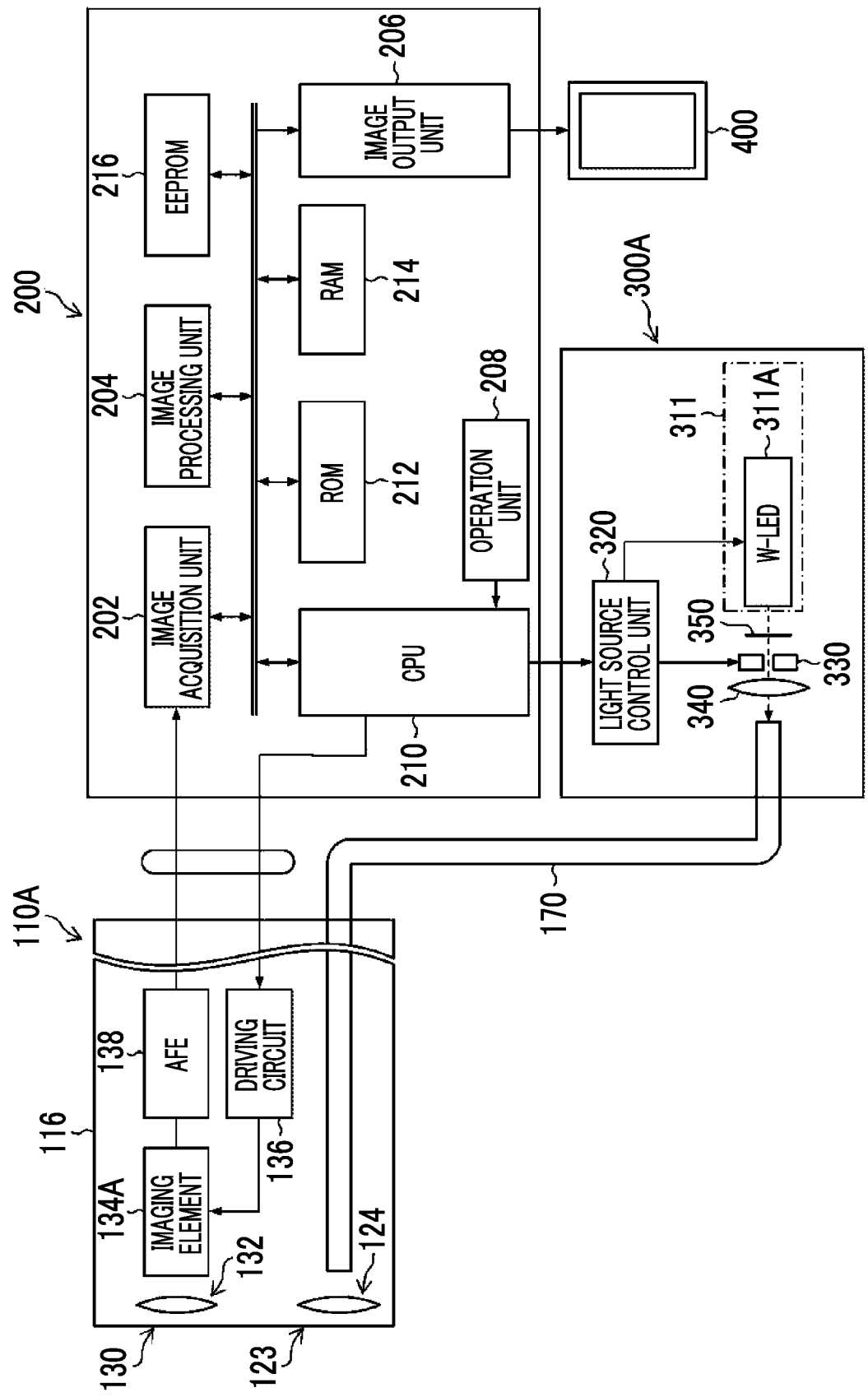
FIG. 17 is a block diagram showing the configuration of a modification example of an endoscope system.
Figure 18:
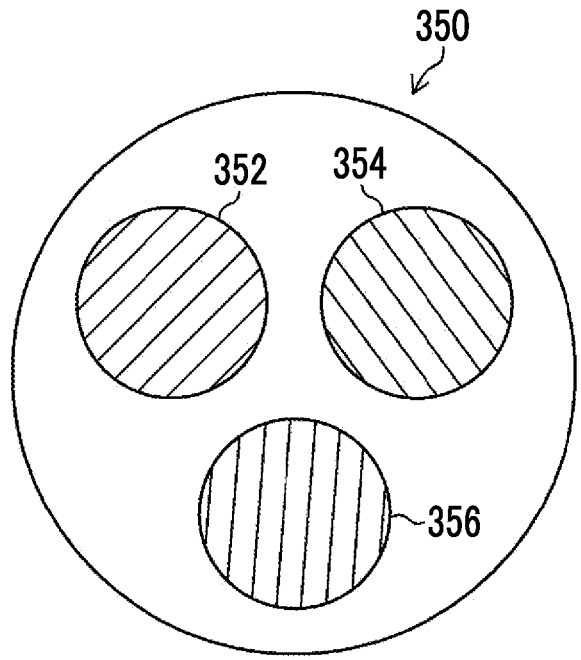
FIG. 18 is a diagram showing a rotary filter in the modification example.

In the modification example shown in FIG. 17, a light source device 300A includes a white light emitting diode (W-LED) 311A that emits white light as a light source 311, and a rotary filter 350 shown in FIG. 18 is provided before the W-LED 311A. A red color filter 352 (band pass filter), a blue color filter 354 (band pass filter), and a green color filter 356 (band pass filter) are provided in the rotary filter 350. By rotating the rotary filter 350 so that white observation light is transmitted through the color filter 352, 354, or 356, it is possible to emit red, blue, or green observation light. Then, every time the observation light of each color is emitted, a monochrome imaging element 134A provided in the insertion part 104 performs imaging using a frame sequential method. As a result, imaging signals of red, blue, and green are obtained, and a color image can be generated from the imaging signals of three colors. An image may be generated from imaging signals of one color or two colors of red, blue, and green. A filter, such as the rotary filter 350, may be provided on the front surface of the imaging element 134A instead of the front surface of the W-LED 311A as a light source. Instead of the rotary filter, a color filter (color filter in which any one of R, G, and B color filters is provided for each pixel) similar to that in the first embodiment may be provided on the front surface of the imaging element 134A. As described above, also in this modification example, it is possible to acquire a plurality of images having different ranges of observation light.

Second Embodiment

Figure 19:
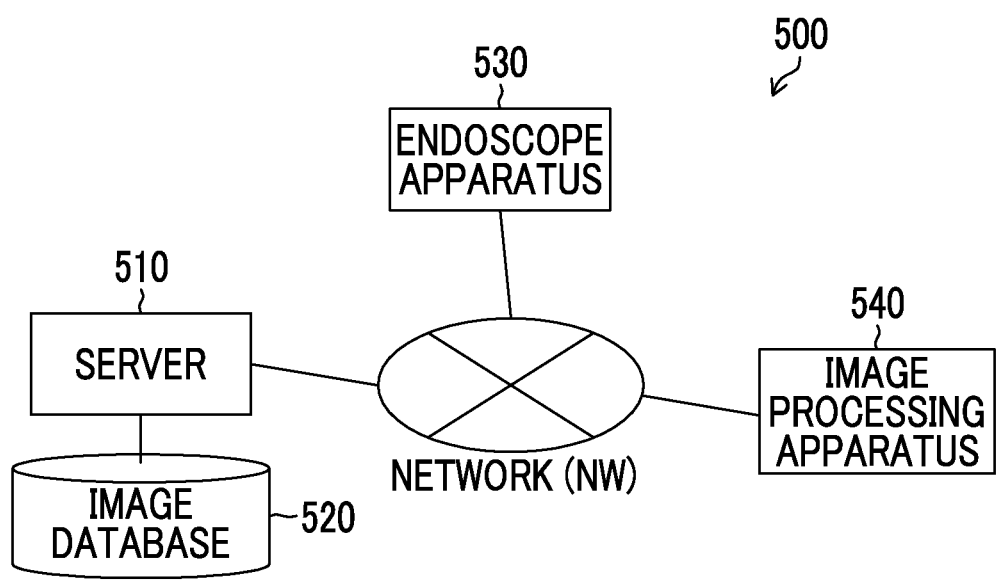
FIG. 19 is a diagram showing the configuration of an image processing system according to a second embodiment of the present invention.

Next, a second embodiment of the present invention will be described. FIG. 19 is a diagram showing the configuration of a medical image processing system 500 according to a second embodiment. The medical image processing system 500 includes a server 510, an image database 520, an endoscope apparatus 530, an image processing apparatus 540, and a network NW that connects these to each other.

The server 510 controls transmission and reception and recording of images, and images are recorded in the image database 520 under the control of the server 510. The endoscope apparatus 530 captures an image of the subject (living body) with a light source device (not shown) and an imaging unit (not shown) similar to those in the endoscope system 10 according to the first embodiment. The image processing apparatus 540 corresponds to the endoscope processor 200 in the first embodiment, processes the image acquired from the image database 520 to perform processing, such as estimation of blood vessel information. The image processing apparatus 540 is an example of the image processing apparatus of the present invention, and is configured to include, for example, a computer and a program running on the computer (image processing program causing the image processing apparatus to execute an image processing method according to the present invention).

Figure 20:
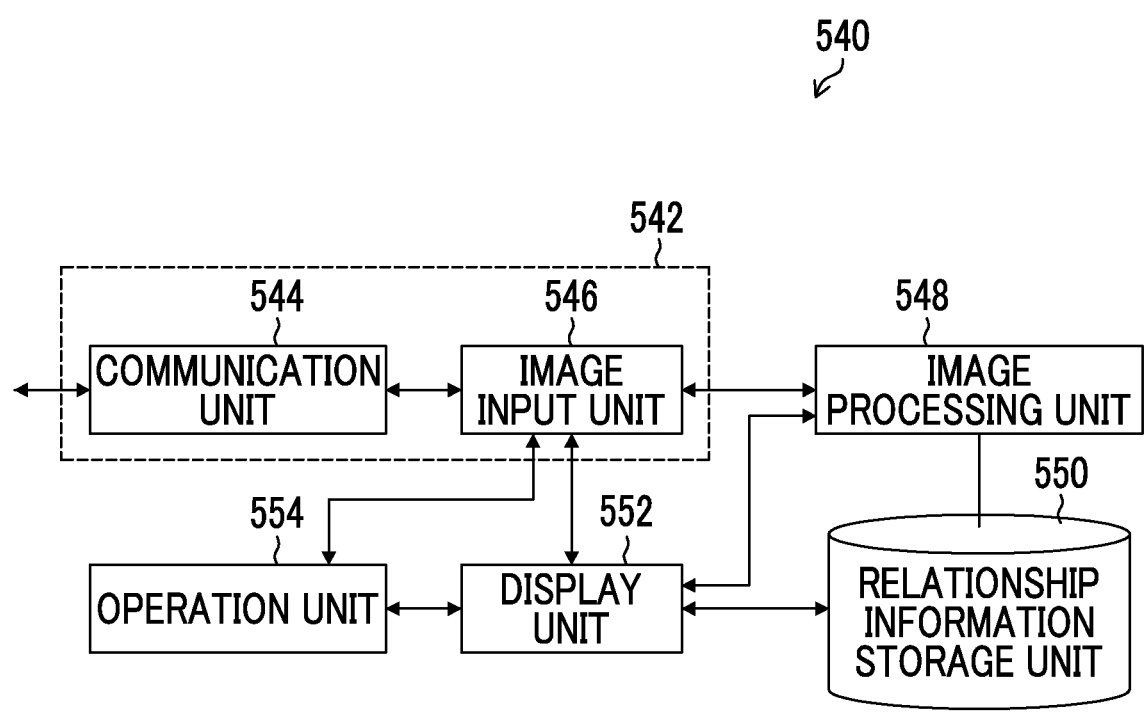
FIG. 20 is a block diagram showing the configuration of an image processing apparatus in the second embodiment.

FIG. 20 is a block diagram showing the schematic configuration of the image processing apparatus 540. As shown in FIG. 20, the image processing apparatus 540 includes: a communication unit 544 that communicates with the server 510 and the endoscope apparatus 530 through the network NW; an image input unit 546 that controls the communication unit 544 to input an image; an image processing unit 548 (a blood vessel selection unit, a blood vessel index value calculation unit, a blood vessel density calculation unit, a blood vessel index value correction unit, and a blood vessel information estimation unit) that processes an acquired image to perform estimation of blood vessel information and the like; a relationship information storage unit 550 that stores relationship information (refer to FIGS. 13 and 16) referred to by the image processing unit 548 during processing; a display unit 552 on which information required for medical image processing and processing results are displayed; and an operation unit 554 (blood vessel selection unit) for the user to input information required for processing, such as image acquisition or blood vessel information estimation. These are connected to each other so that the required information can be transmitted and received. The communication unit 544 and the image input unit 546 form an image acquisition unit 542. In the second embodiment, the range information of the observation light, which is recorded in the header of the image file, may be acquired together with the image. Alternatively, the range information of the observation light may be acquired separately from the image database 520 or the endoscope apparatus 530.

The function of each unit of the image processing apparatus 540 can be realized, for example, by a control device such as a central processing unit (CPU) executing an image processing program stored in storage means (non-transitory recording medium), such as a ROM. As a result, the image processing method (refer to FIG. 6) according to the present invention is executed. The communication unit 544 includes an antenna for wireless communication and an input and output interface circuit, and the relationship information storage unit 550 includes a recording device, such as a hard disk drive (HDD). The display unit 552 includes a display device, such as a liquid crystal display, and the operation unit 554 includes an input and operation device, such as a keyboard and a mouse. These are examples of the configuration of the image processing apparatus 540 according to the second embodiment, and other configurations can be appropriately adopted.

Also in the image processing apparatus 540 having the above-described configuration, similarly to the endoscope system 10 according to the first embodiment, it is possible to accurately estimate blood vessel information, such as the blood vessel depth, the blood vessel thickness, and the oxygen saturation, and it is possible to present information useful for diagnosis.

Although the embodiments and modification examples of the present invention have been described above, the present invention is not limited to these embodiments and modification examples, and various modifications can be made without departing from the spirit of the present invention.

EXPLANATION OF REFERENCES

10: endoscope system
100: endoscope apparatus
102: hand operation portion
104: insertion part
106: universal cable
108: light guide connector
110: endoscope main body
112: soft portion
114: bending portion
116: distal end rigid portion
116A: distal end side end surface
123: illumination unit
124: observation light lens
126: forceps port
130: imaging optical system
132: imaging lens
134: imaging element
134A: imaging element
136: driving circuit
170: light guide
200: endoscope processor
202: image acquisition unit
204 image processing unit
204A: blood vessel selection unit
204B: blood vessel index value calculation unit
204C: blood vessel density calculation unit
204D: blood vessel index value correction unit
204E: blood vessel information estimation unit
206: image output unit
208: operation unit
210: CPU
216: EEPROM
300: light source device
300A: light source device
310: light source
311: light source
311A: W-LED
320: light source control unit
330: stop 340: condensing lens
350: rotary filter
352: color filter
354: color filter
356: color filter
400: monitor
500: medical image processing system
510: server
520: image database
530: endoscope apparatus
540: image processing apparatus
542: image acquisition unit
544: communication unit
546: image input unit
548: image processing unit
550: relationship information storage unit
552: display unit
554: operation unit
R-CF: R color filter
B-CF: B color filter
G-CF: G color filter
BV1: blood vessel
BV2: blood vessel
BV3: blood vessel
BV4: blood vessel
NW: network
PR1: brightness value
PR3: brightness value
R-L2: relationship information
B-L2: relationship information
G-L2: relationship information
R1: region
S100 to S150: each step of image processing method
i0: image
i1: image
i2: image

What is claimed is:

1. An image processing apparatus, comprising
a non-transitory storage medium; and
a processor coupled to the non-transitory storage medium and configured to:
acquire an image of a living body;
calculate a blood vessel index value of the living body from the acquired image;
calculate a blood vessel density of the living body from the acquired image;
correct the calculated blood vessel index value according to the calculated blood vessel density; and
estimate blood vessel information of the living body based on the corrected blood vessel index value, wherein
the non-transitory storage medium is configured to store relationship information indicating a relationship between the blood vessel density and the blood vessel index value,
the processor is further configured to correct the calculated blood vessel index value based on the stored relationship information;
the calculated blood vessel index value is corrected by adding a correction amount, in which the correction amount increases as the blood vessel density increases, and a slope of the correction amount over the blood vessel density decreases as the blood vessel density increases,
the slope of the correction amount over the blood vessel density represents a slope of a variation amount over the blood vessel density.

2. The image processing apparatus according to claim 1, wherein the non-transitory storage medium is further configured to store relationship information corresponding to a range of observation light emitted to the living body,
the processor is further configured to acquire range information indicating the range of the observation light at the time of capturing the image, and
correct the blood vessel index value based on relationship information that is selected from the stored relationship information based on the acquired range information.

3. The image processing apparatus according to claim 1, wherein the processor is further configured to acquire a plurality of images having different ranges of observation light emitted to the living body, and
calculate the blood vessel index value using the plurality of acquired images.

4. The image processing apparatus according to claim 2, wherein the processor is further configured to acquire a plurality of images having different ranges of observation light emitted to the living body, and
calculate the blood vessel index value using the plurality of acquired images.

5. The image processing apparatus according to claim 1, wherein the processor is further configured to select a target blood vessel, for which the blood vessel index value is to be calculated, in the acquired image,
wherein the processor selects the target blood vessel based on a user's instruction input for the acquired image.

6. The image processing apparatus according to claim 2, wherein the processor is further configured to select a target blood vessel, for which the blood vessel index value is to be calculated, in the acquired image.

7. The image processing apparatus according to claim 3, wherein the processor is further configured to select a target blood vessel, for which the blood vessel index value is to be calculated, in the acquired image.

8. The image processing apparatus according to claim 6, wherein the processor selects the target blood vessel based on a user's instruction input for the acquired image.

9. The image processing apparatus according to claim 7, wherein the processor selects the target blood vessel based on a user's instruction input for the acquired image.

10. The image processing apparatus according to claim 1, wherein the blood vessel index value includes at least one of a contrast of a blood vessel of the living body, a brightness value of a blood vessel portion, or color information of a blood vessel portion.

11. The image processing apparatus according to claim 2, wherein the blood vessel index value includes at least one of a contrast of a blood vessel of the living body, a brightness value of a blood vessel portion, or color information of a blood vessel portion.

12. The image processing apparatus according to claim 3, wherein the blood vessel index value includes at least one of a contrast of a blood vessel of the living body, a brightness value of a blood vessel portion, or color information of a blood vessel portion.

13. The image processing apparatus according to claim 4, wherein the blood vessel index value includes at least one of a contrast of a blood vessel of the living body, a brightness value of a blood vessel portion, or color information of a blood vessel portion.

14. The image processing apparatus according to claim 5, wherein the blood vessel index value includes at least one of a contrast of a blood vessel of the living body, a brightness value of a blood vessel portion, or color information of a blood vessel portion.

15. The image processing apparatus according to claim 1, wherein the blood vessel information includes at least one of a depth of a blood vessel of the living body, a thickness of a blood vessel, a blood volume, or an oxygen saturation of a blood vessel.

16. An image processing apparatus, comprising
a non-transitory storage medium; and
a processor coupled to the non-transitory storage medium and configured to:
acquire a plurality of images having different ranges of observation light emitted to the living body and range information indicating the range of the observation light at the time of capturing the plurality of images;
calculate a blood vessel index value of the living body from the acquired images;
calculate a blood vessel density of the living body from the acquired images;
correct the calculated blood vessel index value according to the calculated blood vessel density; and
estimate blood vessel information of the living body based on a corrected blood vessel index value, wherein
the non-transitory storage medium is configured to store relationship information indicating a relationship between the blood vessel density and the blood vessel index value, and store relationship information corresponding to a range of observation light emitted to the living body,
the processor is further configured to correct the blood vessel index value based on relationship information that is selected from the stored relationship information based on the acquired range information, and estimate blood vessel information of the living body based on the corrected blood vessel index value;
the calculated blood vessel index value is corrected by adding a correction amount, in which the correction amount increases as the blood vessel density increases, and a slope of the correction amount over the blood vessel density decreases as the blood vessel density increases,
the slope of the correction amount over the blood vessel density represents a slope of a variation amount over the blood vessel density.

17. An endoscope system, comprising:
a light source that emits observation light to a living body;
an endoscope main body that captures an image of the living body under the emitted observation light; and
the image processing apparatus according to claim 1,
wherein the image processing apparatus acquires the image captured by the endoscope main body.

18. An image processing method, comprising:
an image acquisition step of acquiring an image of a living body;
a blood vessel index value calculation step of calculating a blood vessel index value of the living body from the acquired image;
a blood vessel density calculation step of calculating a blood vessel density of the living body from the acquired image;
a blood vessel index value correction step of correcting the calculated blood vessel index value according to the calculated blood vessel density; and
a blood vessel information estimation step of estimating blood vessel information of the living body based on the corrected blood vessel index value, wherein
the calculated blood vessel index value is corrected by adding a correction amount, in which the correction amount increases as the blood vessel density increases, and a slope of the correction amount over the blood vessel density decreases as the blood vessel density increases,
the slope of the correction amount over the blood vessel density represents a slope of a variation amount over the blood vessel density.

19. A non-transitory recording medium on which an executable computer readable code is configured to be executed by an image processing apparatus to perform the image processing method of claim 18 is recorded.

* * * * *